(12) United States Patent
Nakatsugawa

(10) Patent No.: US 12,119,122 B2
(45) Date of Patent: Oct. 15, 2024

(54) INFECTION RISK MAPPING DEVICE, METHOD, AND COMPUTER-READABLE STORAGE MEDIUM

(71) Applicant: FUJIFILM Corporation, Tokyo (JP)

(72) Inventor: Haruyasu Nakatsugawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 88 days.

(21) Appl. No.: 17/942,682

(22) Filed: Sep. 12, 2022

(65) Prior Publication Data

US 2023/0094532 A1    Mar. 30, 2023

(30) Foreign Application Priority Data

Sep. 28, 2021   (JP) ................. 2021-158358

(51) Int. Cl.
*G16H 50/80* (2018.01)
*G06Q 50/10* (2012.01)
*G16H 10/60* (2018.01)
*G16H 50/30* (2018.01)

(52) U.S. Cl.
CPC ............. *G16H 50/80* (2018.01); *G06Q 50/10* (2013.01); *G16H 10/60* (2018.01); *G16H 50/30* (2018.01)

(58) Field of Classification Search
CPC ........ G16H 50/80; G16H 10/60; G16H 50/30; G06Q 50/10
See application file for complete search history.

(56) References Cited

U.S. PATENT DOCUMENTS

| 11,342,051 B1 * | 5/2022 | Jain ................. G16H 10/60 |
| 2023/0197289 A1 * | 6/2023 | deLaubenfels ........ G16H 50/80 705/2 |

FOREIGN PATENT DOCUMENTS

| JP | 2015-161987 A | 9/2015 |
| JP | 6107278 B2 * | 4/2017 |
| JP | 6875594 B1 | 5/2021 |

* cited by examiner

*Primary Examiner* — Curtis A Kuntz
*Assistant Examiner* — James E Munion
(74) *Attorney, Agent, or Firm* — Birch, Stewart, Kolasch & Birch, LLP

(57) ABSTRACT

An information processing device includes at least one processor, in which the processor acquires position information and vital information of a user, determines whether or not the user is an infection risk person who has a probability of infection with an infectious disease, on the basis of the vital information, specifies, in a case where the user is determined to be the infection risk person, an infection risk place where there is a probability that the user is infected by the other person or infects the other person, on the basis of the position information, and distinguishably maps the infection risk place specified for the infection risk person and the infection risk place specified in advance for a confirmed infected person with the infectious disease.

19 Claims, 9 Drawing Sheets

DAYS FROM ONSET DATE

FIG. 6

| No. | TIME INFORMATION | POSITION INFORMATION | INFECTION RISK |
|---|---|---|---|
| 1 | 9/1/2021 0:00(T0)-8:30 | HOME | - |
| 2 | 9/1/2021 9:00-18:00 | WORKPLACE | - |
| 3 | 9/1/2021 18:30-20:00 | P RESTAURANT | THERE IS RISK (HIGH RISK) |
| 4 | 9/1/2021 20:30-23:59 | HOME | - |
| 5 | 9/2/2021 0:00-8:30 | HOME | - |
| 6 | 9/2/2021 9:00-18:00 | WORKPLACE | - |
| 7 | 9/2/2021 18:30-23:59 | HOME | - |
| 8 | 9/3/2021 0:00-8:30 | HOME | - |
| 9 | 9/3/2021 9:00-18:00 | WORKPLACE | - |
| 10 | 9/3/2021 18:30-23:59 | HOME | - |
| 11 | 9/4/2021 0:00-10:00 | HOME | - |
| 12 | 9/4/2021 10:30-12:30 | Q PARK | - |
| 13 | 9/4/2021 13:00-14:00 | R RESTAURANT | THERE IS RISK (HIGH RISK) |
| 14 | 9/4/2021 14:30-16:00 | S BOOKSTORE | THERE IS RISK (LOW RISK) |
| 15 | 9/4/2021 16:10-16:20 | T SUPERMARKET | - |
| 16 | 9/4/2021 17:00-23:59 | HOME | - |
| 17 | 9/5/2021 0:00-23:59(T2) | HOME | - |

INFECTION RISK MAPPING DEVICE, METHOD, AND COMPUTER-READABLE STORAGE MEDIUM

CROSS-REFERENCE TO RELATED APPLICATIONS

The present application claims priority under 35 U.S.C. § 119 to Japanese Patent Application No. 2021-158358 filed on Sep. 28, 2021. The above application is hereby expressly incorporated by reference, in its entirety, into the present application.

BACKGROUND OF THE INVENTION

1. Field of the Invention

The present disclosure relates to an information processing device, an information processing method, and an information processing program.

2. Description of the Related Art

Conventionally, a technique for determining a user's infection risk with an infectious disease is known for the purpose of preventing the infection spread of the infectious disease. For example, JP2015-161987A discloses that position information and health information regarding a plurality of users are collected, and an infection risk map that defines the infection risk to be higher in places where many users infected with the disease stay is generated for each place. In addition, JP2015-161987A discloses that the infection risk map is collated with a movement route of a certain user, and a notification of the infection risk in the movement route is given.

Further, for example, JP6875594B discloses that a risk level of an infectious disease is determined on the basis of a contact status with another person, a behavior history of a user, a health condition of the user, and a determination criterion for determining the risk level of the infectious disease.

SUMMARY OF THE INVENTION

The new coronavirus infectious disease (COVID-19), which has been prevalent in recent years, is known to have characteristics that COVID-19 may not develop even if infected and may have an incubation period of several days from infection to onset. Due to these characteristics, the spread of infection by an asymptomatic pathogen carrier who does not develop the disease even if infected and an infected person who is in the incubation period (hereinafter, collectively referred to as "asymptomatic person") has become a problem. In order to prevent the spread of infection more effectively, a technique capable of specifying a place at the risk of infection is desired in consideration of the existence of the asymptomatic person. However, with the techniques disclosed in JP2015-161987A and JP6875594B, it is not possible to specify a place at the risk of infection in consideration of the existence of the asymptomatic person.

The present disclosure provides an information processing device, an information processing method, and an information processing program capable of contributing to the prevention of the infection spread of an infectious disease.

According to a first aspect of the present disclosure, there is provided an information processing device comprising: at least one processor, in which the processor acquires position information and vital information of a user, determines whether or not the user is an infection risk person who has a probability of infection with an infectious disease, on the basis of the vital information, specifies, in a case where the user is determined to be the infection risk person, an infection risk place where there is a probability that the user is infected by the other person or infects the other person, on the basis of the position information, and distinguishably maps the infection risk place specified for the infection risk person and the infection risk place specified in advance for a confirmed infected person with the infectious disease.

In the first aspect, the infection risk person may be a person who is unaware of a symptom related to the infectious disease.

In the first aspect, the infection risk person may be a person who is tested for the infectious disease and who has a negative test result.

In the first aspect, the infection risk person may be a person who has a history of contact with the confirmed infected person with the infectious disease.

In the first aspect, time information indicating a time when the user has existed at a position indicated by the position information may be added to the position information, and the processor may specify a place where the infection risk person has existed for a predetermined period or longer as the infection risk place related to the infection risk person, on the basis of the position information and the time information.

In the first aspect, time information indicating a time when the user has existed at a position indicated by the position information may be added to the position information, and the processor may change a form of the mapping of the infection risk place specified for the infection risk person according to an elapsed time from a time when the infection risk person has existed at the infection risk place to a current time, on the basis of the time information.

In the first aspect, the processor may acquire a test result on the infectious disease of the user determined to be the infection risk person, and may update, in a case where the user has a positive test result, the mapping of the infection risk place specified for the user to the mapping as the infection risk place of the confirmed infected person.

In the first aspect, the processor may acquire a test result on the infectious disease of the user determined to be the infection risk person, and may cancel, in a case where the user has a negative test result, the mapping of the infection risk place specified for the user.

In the first aspect, the processor may recommend continuing to monitor the vital information in a case where the user is determined to be the infection risk person.

In the first aspect, the processor may give a notification of a test timing for the infectious disease on the basis of the vital information, in a case where the user is determined to be the infection risk person.

In the first aspect, the processor may recommend cleaning the infection risk place.

In the first aspect, the processor may issue a warning in a case where the user approaches the infection risk place, on the basis of the position information.

In the first aspect, the vital information may indicate at least one of a heart rate variability, a heart rate, or an arterial blood oxygen saturation.

According to a second aspect of the present disclosure, there is provided an information processing method comprising: acquiring position information and vital information of a user; determining whether or not the user is an infection risk person who has a probability of infection with an infectious disease, on the basis of the vital information; specifying, in a case where the user is determined to be the infection risk person, an infection risk place where there is a probability that the user is infected by the other person or infects the other person, on the basis of the position information; and distinguishably mapping the infection risk place specified for the infection risk person and the infection risk place specified in advance for a confirmed infected person with the infectious disease.

According to a third aspect of the present disclosure, there is provided an information processing program for causing a computer to execute a process comprising: acquiring position information and vital information of a user; determining whether or not the user is an infection risk person who has a probability of infection with an infectious disease, on the basis of the vital information; specifying, in a case where the user is determined to be the infection risk person, an infection risk place where there is a probability that the user is infected by the other person or infects the other person, on the basis of the position information; and distinguishably mapping the infection risk place specified for the infection risk person and the infection risk place specified in advance for a confirmed infected person with the infectious disease.

According to the above aspects, the information processing device, the information processing method, and the information processing program of the present disclosure can contribute to the prevention of the infection spread of an infectious disease.

BRIEF DESCRIPTION OF THE DRAWINGS

FIG. 6 is a diagram showing an example of position information and time information.

DESCRIPTION OF THE PREFERRED EMBODIMENTS

Hereinafter, examples of embodiments of the technique of the present disclosure will be described in detail with reference to the drawings. First, an example of a configuration of an information processing system 1 according to the present embodiment will be described with reference to FIG. 1. The information processing system 1 is a system that specifies a place at the risk of infection in consideration of the existence of an asymptomatic pathogen carrier who does not develop the disease even if infected and an infected person who is in the incubation period (hereinafter, collectively referred to as "asymptomatic person") in addition to a person who is confirmed to be infected with the infectious disease by a test. This contributes to the prevention of the infection spread of the infectious disease. In the following examples of the embodiments, a description will be given by using the new coronavirus infectious disease (COVID-19) as an example of the infectious disease, but the technique of the present disclosure can be applied to other infectious diseases (for example, influenza virus infection diseases).

Figure 1:
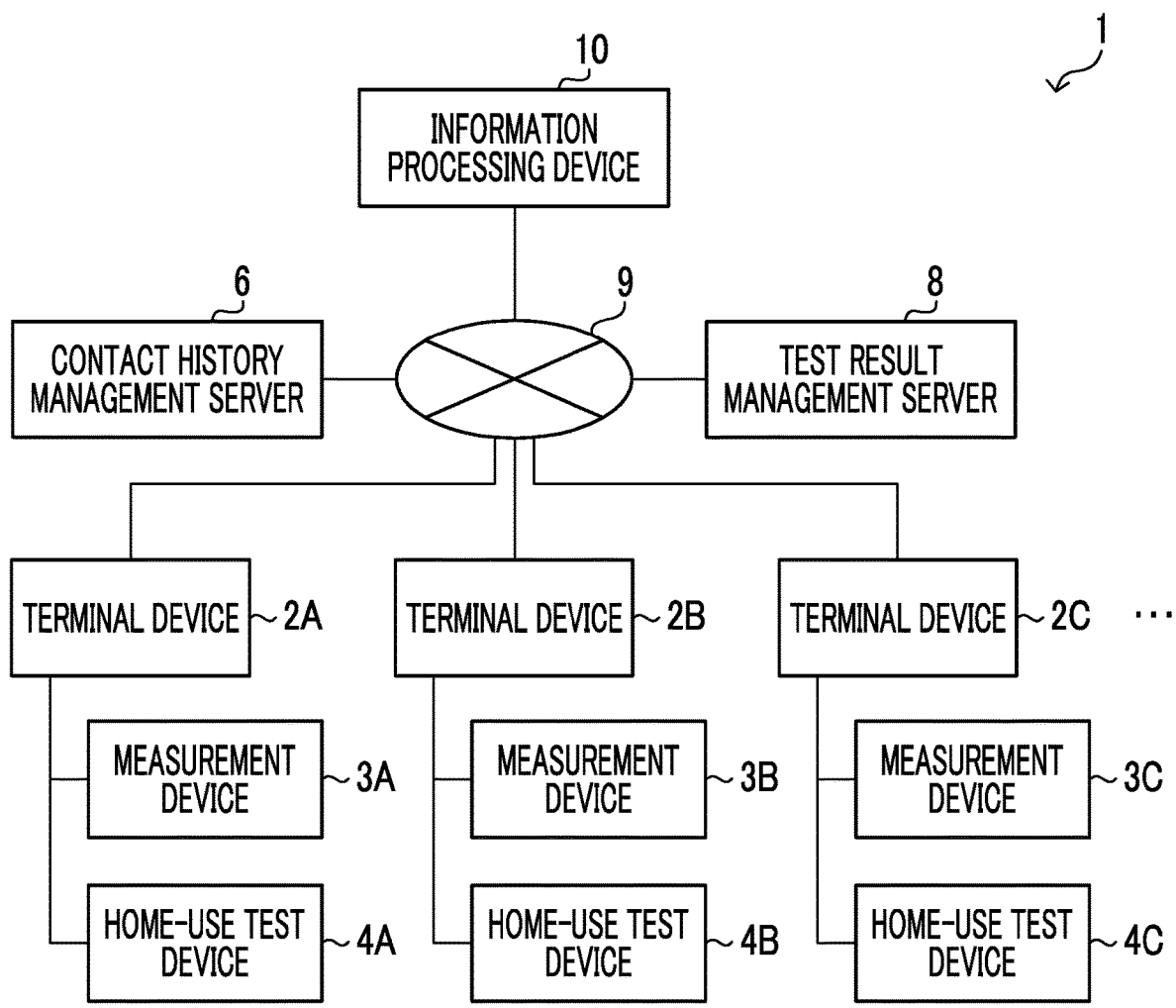
FIG. 1 is a schematic configuration diagram of an information processing system.

As shown in FIG. 1, the information processing system 1 comprises an information processing device 10, a plurality of terminal devices 2A to 2C, a plurality of measurement devices 3A to 3C, a plurality of home-use test devices 4A to 4C, a contact history management server 6, and a test result management server 8. The information processing device 10, the plurality of terminal devices 2A to 2C, the contact history management server 6, and the test result management server 8 can communicate with each other via a wired or wireless network 9.

Hereinafter, the plurality of terminal devices 2A to 2C are simply referred to as "terminal device 2" in a case where the plurality of terminal devices 2A to 2C are not distinguished from each other, the plurality of measurement devices 3A to 3C are simply referred to as "measurement device 3" in a case where the plurality of measurement devices 3A to 3C are not distinguished from each other, and the plurality of home-use test devices 4A to 4C are simply referred to as "home-use test device 4" in a case where the plurality of home-use test devices 4A to 4C are not distinguished from each other. FIG. 1 shows three terminal devices 2, three measurement devices 3, and three home-use test devices 4, but the numbers of respective devices provided in the information processing system 1 are not particularly limited.

In the information processing system 1, it is assumed that each of a plurality of users owns the terminal device 2, the measurement device 3, and the home-use test device 4. That is, an owner of the terminal device 2A, the measurement device 3A, and the home-use test device 4A, an owner of the terminal device 2B, the measurement device 3B, and the home-use test device 4B, and an owner of the terminal device 2C, the measurement device 3C, and the home-use test device 4C are users different from each other. The terminal device 2 is connected to the measurement device 3 and the home-use test device 4 owned by the same user by wireless or wired communication. As the standard of the wireless communication in this case, for example, Wi-Fi (registered trademark) and Bluetooth (registered trademark) can be appropriately applied.

The measurement device 3 measures at least one type of vital information of the user over time, and transmits the measured vital information to the terminal device 2 by wired or wireless communication. "Measurement over time" means that the vital information is continuously measured at a predetermined time interval. The vital information is, for example, information indicating at least one of a heart rate variability, a heart rate, or an arterial blood oxygen saturation (SpO2). As the measurement device 3, for example, a heart rate meter and a wearable terminal, such as a smartwatch provided with a sensor that measures vital information, can be applied. Further, a plurality of measurement devices 3 that measure different types of vital information may be connected to one terminal device 2.

The home-use test device 4 carries out a self-test as to whether or not the user is infected with the infectious disease, and transmits the test result to the terminal device 2 by wired or wireless communication. As the home-use test device 4, for example, a home-use COVID-19 antigen test kit manufactured by Ellume Limited can be applied.

The contact history management server 6 uses a known COVID-19 contact confirmation application to notify the terminal device 2 that the user who is the owner of the terminal device 2 has a contact probability with an infected person with COVID-19, in a case where the user has a contact probability with the infected person. Here, "contact" with an infected person means that the infected person exists within a predetermined distance from a position where the user exists, during a period when the infected person is infectious to the other person, and includes so-called "close contact". As the contact history management server 6, for example, a server computer or a personal computer can be applied.

The test result management server 8 collects the test result as to whether or not the user is infected with the infectious disease, which is carried out at a medical institution or the like, in association with the user. Examples of the test for the infectious disease carried out at a medical institution or the like include a polymerase chain reaction (PCR) test, an antigen test, an antibody test, and a diagnostic imaging. As the test result management server 8, for example, a server computer or a personal computer can be applied.

The terminal device 2 receives the vital information of the user from the measurement device 3 by wired or wireless communication. Further, the terminal device 2 receives the test result as to whether or not the user is infected with the infectious disease, from the home-use test device 4 by wired or wireless communication. Further, in a case where the received test result is positive, the terminal device 2 may make an appointment for a medical examination with respect to an external device (not shown) installed at a medical institution, or may give a notification of infection with respect to an external device installed at a health center.

Further, the terminal device 2 receives a contact notification that the user has a contact probability with the infected person with COVID-19, from the contact history management server 6 via the network 9. Further, the terminal device 2 uses the Global Positioning System (GPS), Wi-Fi (registered trademark), or the like to collect position information of the user, time information indicating the time when the user has existed at a position indicated by the position information in association with each other (see FIG. 6).

Further, the terminal device 2 transmits the position information, the time information, the vital information, the test result on the infectious disease, the contact notification, and the like to the information processing device 10 via the network 9. The terminal device 2 is a device including a central processing unit (CPU), a read only memory (ROM), a random access memory (RAM), and the like. As the terminal device 2, for example, a smartphone, a personal computer, a tablet terminal, or a wearable terminal can be applied.

Figure 2:
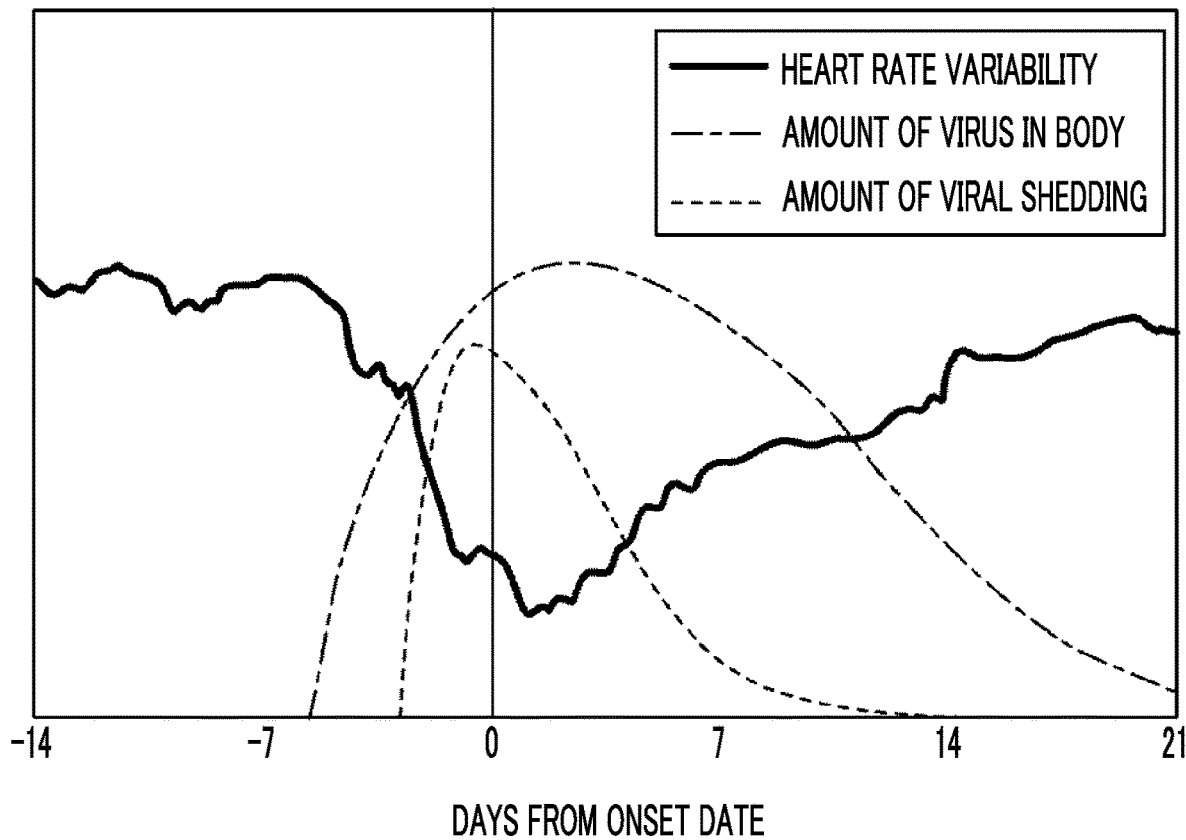
FIG. 2 is a schematic diagram showing changes in heart rate variability and the like of an infected person with COVID-19.

Here, the characteristics of COVID-19 will be described with reference to FIG. 2. FIG. 2 is a schematic diagram showing an example of changes in heart rate variability (HRV) of the infected person with COVID-19, the amount of virus in the body, and the amount of viral shedding. In FIG. 2, the heart rate variability is shown by a solid line, the amount of virus in the body is shown by an alternating long-dash and short-dash line, and the amount of viral shedding is shown by a broken line. In the horizontal axis of FIG. 2, the onset date when the infected person is aware of symptoms such as fever and cough is set as day 0, and the day after the onset is indicated by a day with a plus, and the day before the onset is indicated by a day with a minus.

The heart rate variability is a value representing the changes in the time interval (RRI: R-R Interval) for each beat of the heartbeat. Specifically, the heart rate variability is represented by, for example, a standard deviation of the R-R interval (SDNN) in a predetermined period and/or a root mean square of successive two R-R interval differences (rMSSD).

As shown in FIG. 2, the amount of viral shedding (that is, the degree of infectivity to the other person) emitted from the infected person with COVID-19 rapidly increases from several days before the onset date and peaks before the onset date. That is, COVID-19 has characteristics that COVID-19 has the highest infectivity to the other person during the incubation period from infection to onset. It is also known that some infected persons with COVID-19 are asymptomatic pathogen carriers who do not develop the disease even if infected. Even asymptomatic pathogen carrier may be infectious to the other person.

On the other hand, as shown in FIG. 2, in the infected person with COVID-19, the amount of virus in the body peaks several days after the onset date. Therefore, the test result may be negative (so-called false negative) even in a case where a test using the home-use test device 4, and a PCR test and an antigen test at a medical institution or the like are performed during the incubation period or immediately after the onset.

Further, as shown in FIG. 2, the infected person with COVID-19 has a characteristic that an abnormal tendency, such as a decrease in heart rate variability, is observed during the incubation period. This is because the heart rate increases, for example, at the time of exercise or in a tension state and the heart rate decreases at the time of relaxation in a case of the heart rate variability of an uninfected person, whereas followability of the heartbeat is poor and a degree of increase/decrease in the heart rate is small in a case of the heart rate variability of the infected person. After that, the heart rate variability reaches the minimum value near the onset date and gradually returns to normal over a dozen days. This abnormal tendency in heart rate variability may also be observed in the asymptomatic pathogen carrier and the infected person with the false negative test result.

As described above, the fact that the infected person with COVID-19 shows the abnormal tendency in heart rate variability is used, whereby the information processing device 10 according to the present embodiment detects an infection risk person who has a probability of infection with the infectious disease, for example, including a person who is unaware of symptoms related to the infectious disease, such as the infected person who is in the incubation period and the asymptomatic pathogen carrier, and the infected person with the false negative test result. In addition, an infection risk place where there is a probability that the infection risk person may be infected by the other person or may infect the other person is specified and mapped. "Mapping" is to indicate an infection risk place on a map so that the user can confirm the infection risk place (see FIG. 8).

Further, in a case where the test result obtained by the home-use test device 4 of the user is negative, the information processing device 10 gives a notification of the timing of a retest in the home-use test device 4 or in the medical institution, in consideration of the probability of false negative test result. In that respect, in the following description, a description will be given on the assumption that the user to be processed by the information processing device 10 has already carried out the self-test using the home-use test device 4. Hereinafter, the detailed configuration of the information processing device 10 will be described.

Figure 3:
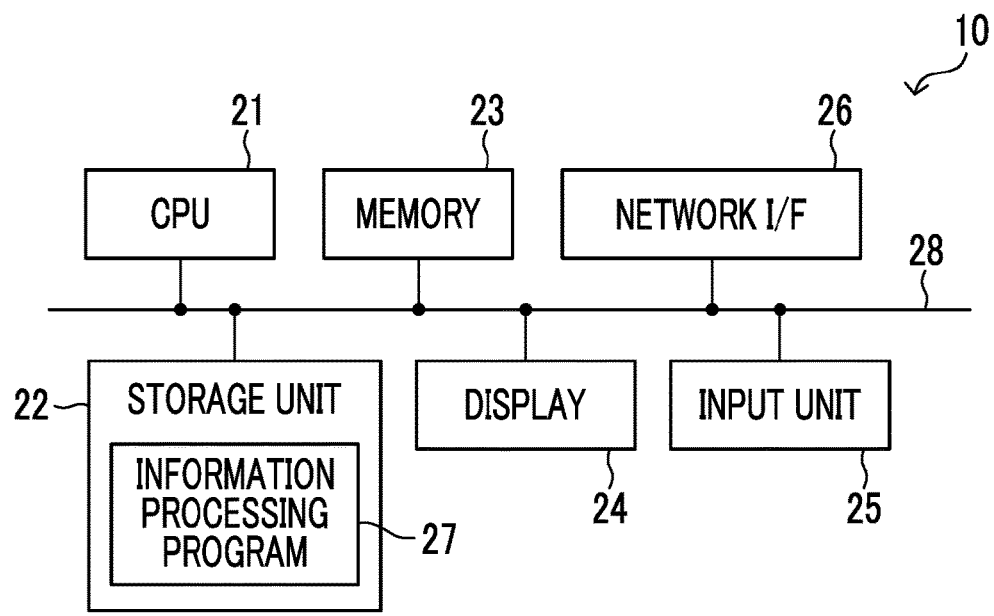
FIG. 3 is a block diagram showing an example of a hardware configuration of an information processing device.

First, an example of a hardware configuration of the information processing device 10 according to the present embodiment will be described with reference to FIG. 3. As shown in FIG. 3, the information processing device 10 includes a CPU 21, a non-volatile storage unit 22, and a memory 23 serving as a temporary storage area. In addition, the information processing device 10 includes a display 24 such as a liquid crystal display, an input unit 25 such as a keyboard, a mouse, and a touch panel, and a network interface (I/F) 26. The network I/F 26 performs wired or wireless communication with the network 9. The CPU 21, the storage unit 22, the memory 23, the display 24, the input unit 25, and the network I/F 26 are connected to each other via a bus 28, such as a system bus and a control bus, so that various types of information can be exchanged.

The storage unit 22 is realized by, for example, a storage medium such as a hard disk drive (HDD), a solid state drive (SSD), and a flash memory. An information processing program 27 in the information processing device 10 is stored in the storage unit 22. The CPU 21 reads out the information processing program 27 from the storage unit 22 and then develops the information processing program 27 into the memory 23, and executes the developed information processing program 27. The CPU 21 is an example of a processor of the present disclosure. As the information processing device 10, for example, a server computer, a personal computer, a smartphone, a tablet terminal, or a wearable terminal can be appropriately applied.

Figure 4:
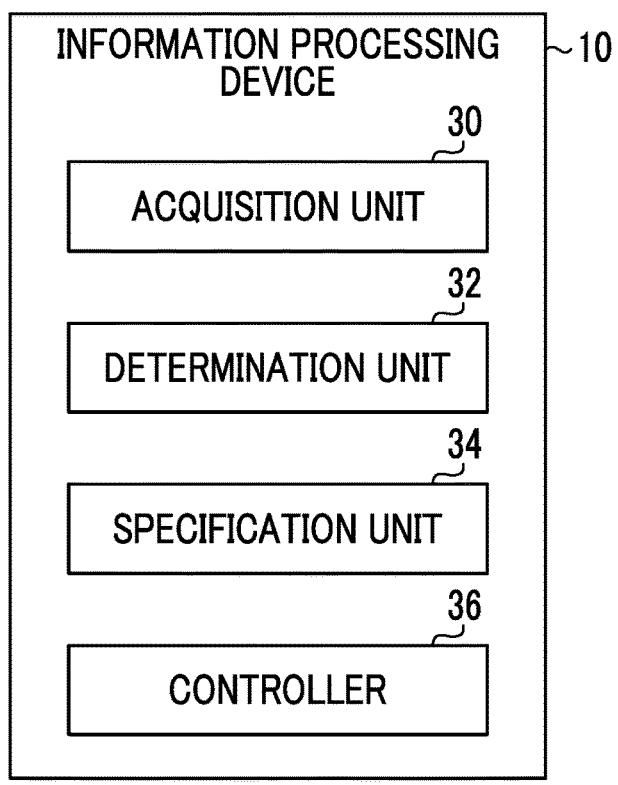
FIG. 4 is a block diagram showing an example of a functional configuration of the information processing device.

Next, an example of a functional configuration of the information processing device 10 according to the present embodiment will be described with reference to FIG. 4. As shown in FIG. 4, the information processing device 10 includes an acquisition unit 30, a determination unit 32, a specification unit 34, and a controller 36. The CPU 21 executes the information processing program 27, whereby the CPU 21 functions as the acquisition unit 30, the determination unit 32, the specification unit 34, and the controller 36.

Specification of Infection Risk Place Related to Infection Risk Person

Figure 5:
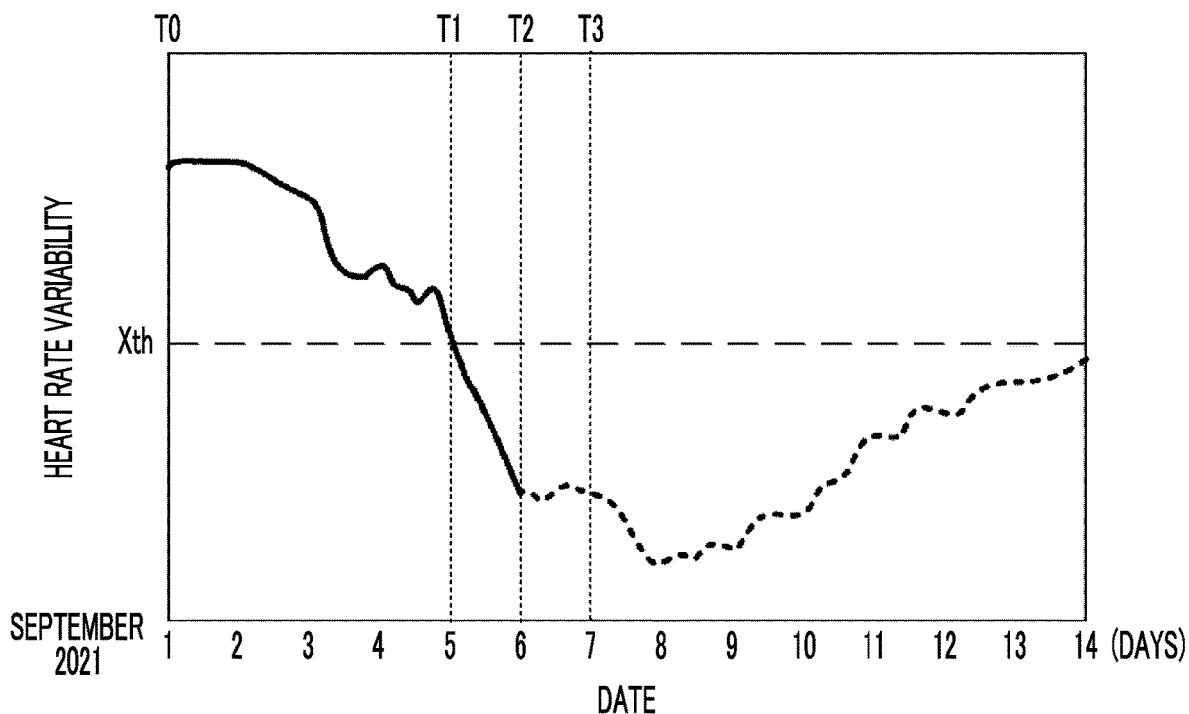
FIG. 5 is a diagram showing an example of the heart rate variability.

The acquisition unit 30 acquires the user's position information and vital information, and the test result obtained by the home-use test device 4, from the terminal device 2 via the network 9. FIG. 5 shows an example of the heart rate variability as an example of the user's vital information acquired by the acquisition unit 30. FIG. 5 is a diagram showing the value of the heart rate variability for each date and shows the same changes as the heart rate variability in FIG. 2, and the onset date (day 0) in FIG. 2 corresponds to timing T3 in FIG. 5. Hereinafter, a description will be given on the assumption that the acquisition unit 30 acquires the heart rate variability in the period from timing T0 to timing T2 in FIG. 5 (the solid line portion in FIG. 5). Timing T2 is, for example, the current time, and timing T0 is, for example, the same time five days before the current time. That is, the acquisition unit 30 acquires the heart rate variability for five days in the incubation period, before timing T3 corresponding to the onset date.

The determination unit 32 determines whether or not the user is the infection risk person who has a probability of infection with the infectious disease, on the basis of the vital information, in a case where the test result obtained by the home-use test device 4 and acquired by the acquisition unit 30 is negative. For example, in a case where there is timing T1 when the value of the heart rate variability acquired by the acquisition unit 30 is a predetermined threshold value Xth or less, the determination unit 32 may determine that the user is the infection risk person because the heart rate variability has the abnormal tendency. The determination unit 32 may determine that the user is the infection risk person in a case where the value of the heart rate variability is the threshold value Xth or less for a predetermined period so as not to regard the temporary decrease in heart rate variability as the abnormal tendency. That is, in the present embodiment, the infection risk person may be a person who is tested for the infectious disease and who has a negative test result.

In a case where the determination unit 32 determines that the user is the infection risk person, the specification unit 34 specifies the infection risk place where there is a probability that the user may be infected by the other person or may infect the other person on the basis of the position information acquired by the acquisition unit 30, and stores the infection risk place in the storage unit 22. Examples of places that can be "infection risk place" include places where an unspecified number of people gather, such as restaurants, retail stores, and tourist spots.

FIG. 6 shows, as an example of the user's position information acquired by the acquisition unit 30, the position information in the period from timing T0 to timing T2, which is the period in which the heart rate variability is acquired, in chronological order. "No." is assigned in chronological order. As shown in FIG. 6, the time information indicating the time when the user has existed at a position indicated by the position information is added to the position information. In the example of FIG. 6, the position information is shown by the place name for the sake of clarity, but the position information may be represented by the latitude and longitude, the identification information predetermined for each place, and the like. Further, in the example of FIG. 6, the description of the position information and the time information during the movement between the places is omitted for the sake of clarity.

Specifically, the specification unit 34 specifies a place where the infection risk person has existed for a predetermined period or longer, as the infection risk place, on the basis of the position information and the time information. In the "infection risk" column of FIG. 6, a place specified as the infection risk place is indicated by "there is risk", and a place that is not the infection risk place is indicated by "−".

For example, the specification unit 34 may specify a place where the user has stayed for 30 minutes or more (90 minutes) as the infection risk place, as shown in "No. 3" of FIG. 6. Further, for example, the specification unit 34 specifies that a place where the user has only stayed for less than 30 minutes (10 minutes) is not the infection risk place, as shown in "No. 15" of FIG. 6.

Further, the specification unit 34 may change the magnitude of the infection risk in a case where a place is specified as the infection risk place, according to the characteristics of the place. For example, the specification unit 34 may determine that the infection risk is high in a case where the restaurant is specified as the infection risk place, as shown in "No. 3" and "No. 13" of FIG. 6. This is because it is considered that the infection risk is high in restaurants due to neglect of the infection control measures using masks when eating and drinking. Further, for example, the specification unit 34 may determine that the infection risk is low even in a case where the place other than the restaurant is specified as the infection risk place, as shown in "No. 14" of FIG. 6.

Further, the specification unit 34 may not specify the infection risk place according to the characteristics of the place. For example, the specification unit 34 may not specify the outdoor area, such as a park, as the infection risk place even in a case where the stay time is a predetermined period or longer, as shown in "No. 12" of FIG. 6. Further, for example, the specification unit 34 may not specify a place where only a specific person stays, such as a home, a workplace, and a school, as the infection risk place, as shown in "No. 1", "No. 2", and the like of FIG. 6.

Follow-Up Observation of Infection Risk Person

In a case where the determination unit 32 determines that the user is the infection risk person, the controller 36 may give a notification to recommend continuing to monitor the vital information, with respect to the terminal device 2 owned by the user. In this case, the CPU 21 may acquire vital information, which is continuously monitored, from the terminal device 2, determine whether or not the user is the infection risk person on the basis of the vital information, and specify the infection risk place on a regular basis.

Further, in a case where the determination unit 32 determines that the user is the infection risk person, the controller 36 may notify the terminal device 2 owned by the user of the test timing for the infectious disease, on the basis of the vital information. As shown in FIG. 2, in the case of the infected person with COVID-19, the accuracy of the test for the infectious disease is improved because the amount of virus in the body is the maximum, at approximately the same time as the time when the value of the heart rate variability is the minimum (that is, the most abnormal tendency is shown). In that respect, for example, the controller 36 may continue to monitor the heart rate variability, and may give a notification to perform the test for the infectious disease at the timing when the heart rate variability is a predetermined threshold value or less. Further, for example, the controller 36 may give a notification to perform the test for the infectious disease at a point in time (for example, three to five days after timing T1) when a predetermined period has elapsed from timing T1 when the value of the heart rate variability is the predetermined threshold value Xth or less.

Further, for example, in a case where the controller 36 continues to monitor the heart rate variability and the heart rate variability returns to normal, the controller 36 may determine that user is not the infection risk person and may delete the infection risk place specified for the user from the storage unit 22.

Figure 7:
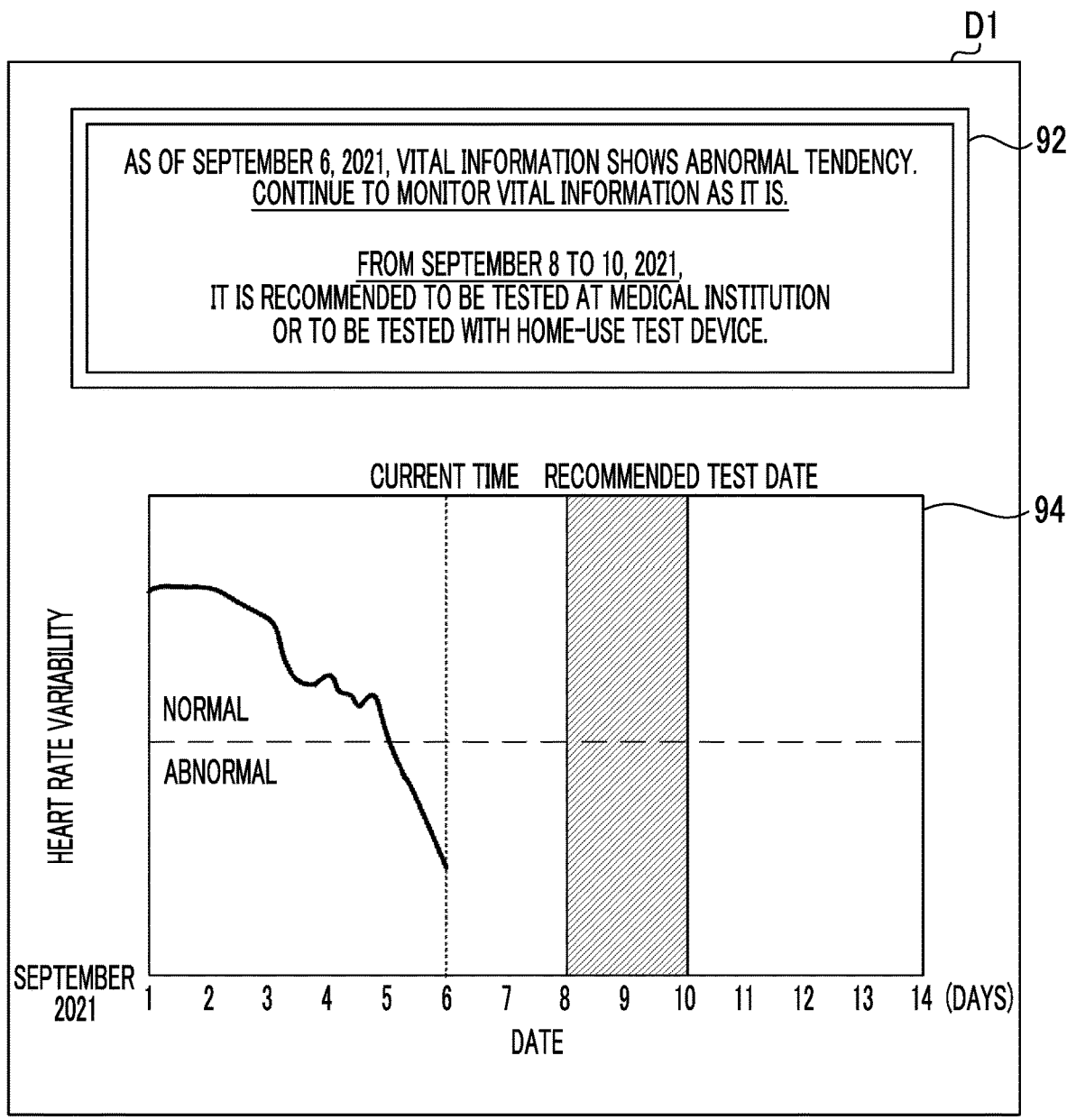
FIG. 7 is a diagram showing an example of a screen displayed on a display.

FIG. 7 shows an example of a screen D1 displayed on a display of the terminal device 2. The screen D1 includes a notification 92 performed by the controller 36 and a notification 94 including a diagram showing the value of the heart rate variability up to the current time. The notification 92 includes a notification to recommend continuing to monitor the vital information and a notification of the test timing for the infectious disease. In this way, since the test is encouraged to be performed at an appropriate timing so that an accurate test result can be also obtained for the infected person who is in the incubation period, the asymptomatic pathogen carrier, and the infected person with the false negative test result due to the test performed in the early stage of infection, it is possible to contribute to the prevention of the infection spread of the infectious disease.

Specification of Infection Risk Place Related to Confirmed Infected Person

In a case where the test result obtained by the home-use test device 4 and acquired by the acquisition unit 30 is positive, the specification unit 34 specifies the infection risk place as the confirmed infected person, on the basis of the position information and the time information, and stores the infection risk place in the storage unit 22.

Further, in a case where the infection risk person is later changed to the confirmed infected person, the CPU 21 changes the infection risk place to the infection risk place as the confirmed infected person. Specifically, the acquisition unit 30 acquires the test result on the infectious disease of the user determined to be the infection risk person, from the home-use test device 4 or the test result management server 8. That is, as described above, this test result is obtained at an appropriate timing of which the terminal device 2 is notified by the controller 36.

In a case where the test result acquired by the acquisition unit 30 for the user determined to be the infection risk person is positive, the specification unit 34 re-specifies the infection risk place specified for the user (that is, the infection risk person) as the infection risk place of the confirmed infected person, and stores the infection risk place in the storage unit 22. On the other hand, in a case where the test result acquired by the acquisition unit 30 for the user determined to be the infection risk person is negative, the specification unit 34 re-specifies that the infection risk place specified for the user (that is, the infection risk person) is not the infection risk place, and delete the infection risk place from the storage unit 22.

The CPU 21 performs the above processing performed by the acquisition unit 30, the determination unit 32, the specification unit 34, and the controller 36, for each of the plurality of users. With this, the storage unit 22 accumulates information on infection risk places related to a plurality of infection risk persons and information on infection risk places related to a plurality of confirmed infected persons, in the latest state.

Mapping of Infection Risk Place

The controller 36 distinguishably maps the infection risk place specified for the infection risk person and the infection risk place specified in advance for the confirmed infected person with the infectious disease, which are accumulated in the storage unit 22. "Distinguishably mapping" may be realized by, for example, making the forms of a figure, such as the shape, size, color, and line type, different between the infection risk person and the confirmed infected person, in a case where the infection risk place is shown as the figure on a map.

Figure 8:
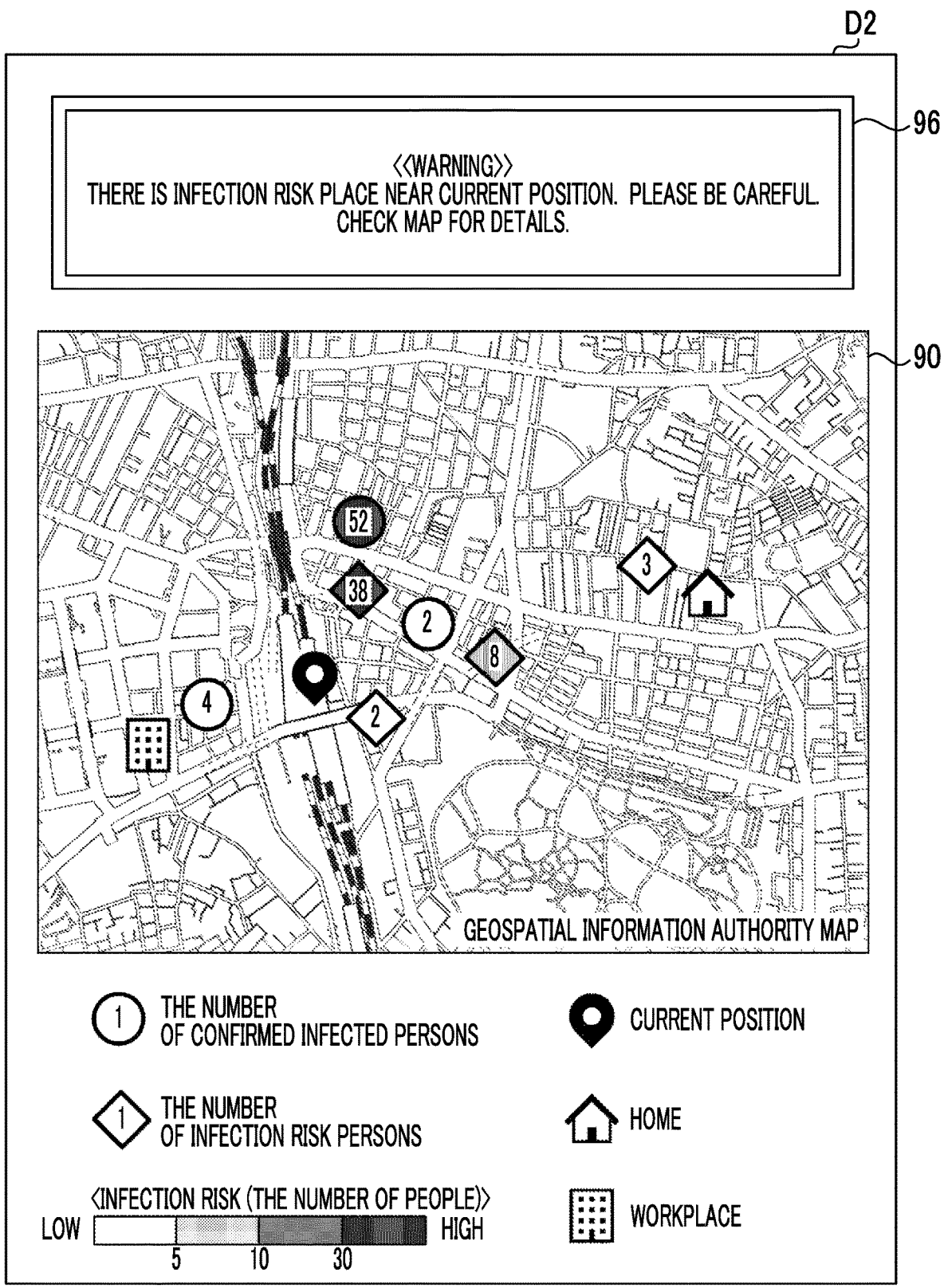
FIG. 8 is a diagram showing an example of the screen displayed on the display.

FIG. 8 shows an example of a screen D2 including a map 90 to which the infection risk place is mapped. The screen D2 is a screen that is controlled so as to be displayed on the display of the terminal device 2 by the controller 36, in a case where there is a request from the terminal device 2. As shown on the map 90, the controller 36 may map the infection risk places by using different figures between the infection risk person (shown by a diamond) and the confirmed infected person (shown by a circle).

Further, as shown on the map 90, the controller 36 may change the form of mapping the infection risk place according to the number of confirmed infected persons or infection risk persons, for each infection risk place. In this case, since it is considered that the infection risk is higher as the number of people increases, it is preferable to emphasize and map the infection risk place as the number of people increases. In FIG. 8, the mapping is made such that the background color of the figure becomes darker as the number of confirmed infected persons or infection risk persons for each infection risk place increases.

Further, the controller 36 also updates the mapping each time the information on the infection risk place accumulated in the storage unit 22 is updated. For example, in a case where the acquisition unit 30 acquires a test result showing a positive result for the user determined to be the infection risk person, the controller 36 updates the mapping of the infection risk place specified for the user to the mapping as the infection risk place of the confirmed infected person. Alternatively, for example, in a case where the acquisition unit 30 acquires a test result showing a negative result for the user determined to be the infection risk person, the controller 36 cancels the mapping of the infection risk place specified for the user.

Further, as shown in FIG. 8, the controller 36 may perform control to issue a warning 96 to the terminal device 2 in a case where the user approaches the infection risk place, on the basis of the user's position information at the current time. According to such an aspect, the user can avoid the infection risk place, so that it is possible to contribute to the prevention of the infection spread of the infectious disease.

Figure 9:
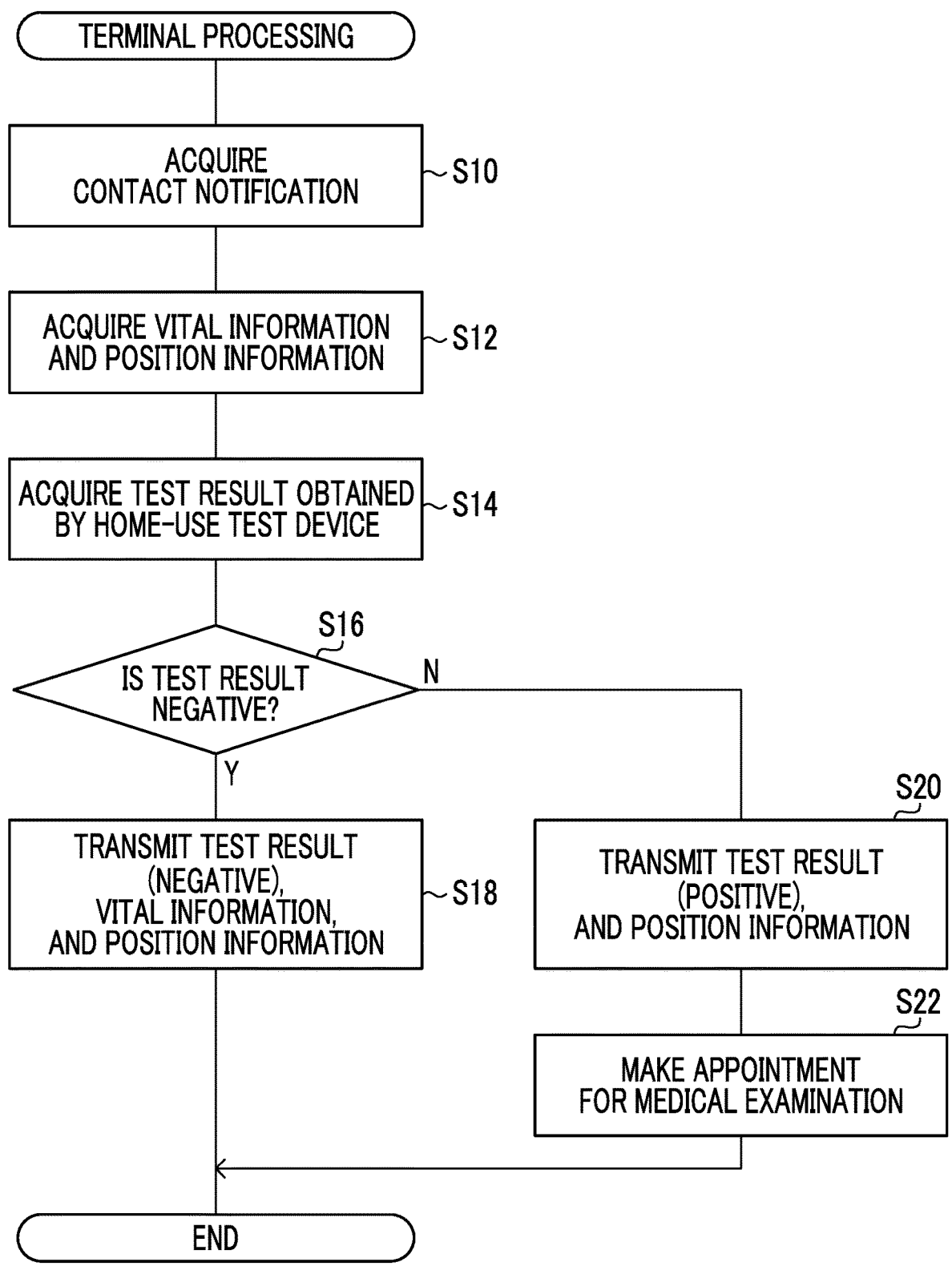
FIG. 9 is a flowchart showing an example of terminal processing in a terminal device.

Next, an action of the terminal device 2 according to the present embodiment will be described with reference to FIG. 9. In the terminal device 2, the CPU executes an information processing program, whereby terminal processing shown in FIG. 9 is executed. The execution of the terminal processing starts, for example, in a case where a contact notification that the user has a contact probability with the infected person with COVID-19 is received from the contact history management server 6 (corresponding to step S10).

In step S10, the terminal device 2 receives a contact notification that the user has a contact probability with the infected person with COVID-19, from the contact history management server 6. In step S12, the terminal device 2 acquires the vital information of the user from the measurement device 3. Further, the terminal device 2 acquires the user's position information and time information in association with each other. In step S14, the terminal device 2 receives the test result as to whether or not the user is infected with the infectious disease, from the home-use test device 4 by wired or wireless communication.

In step S16, the terminal device 2 determines whether or not the test result received in step S14 is negative. In a case where the test result is negative (that is, in a case where step S16 is Y), in step S18, the terminal device 2 transmits the test result showing the negative test result received in step S14, and the position information to which the time information is added and the vital information, which are acquired in step S12, to the information processing device 10, and ends the terminal processing.

On the other hand, in a case where the test result is positive (that is, in a case where step S16 is N), in step S20, the terminal device 2 transmits the test result showing the positive test result received in step S14 and the position information to which the time information is added, which is acquired in step S12, to the information processing device 10. In step S22, the terminal device 2 makes an appointment for a medical examination with respect to an external device installed in the medical institution, and ends the terminal processing.

Figure 10:
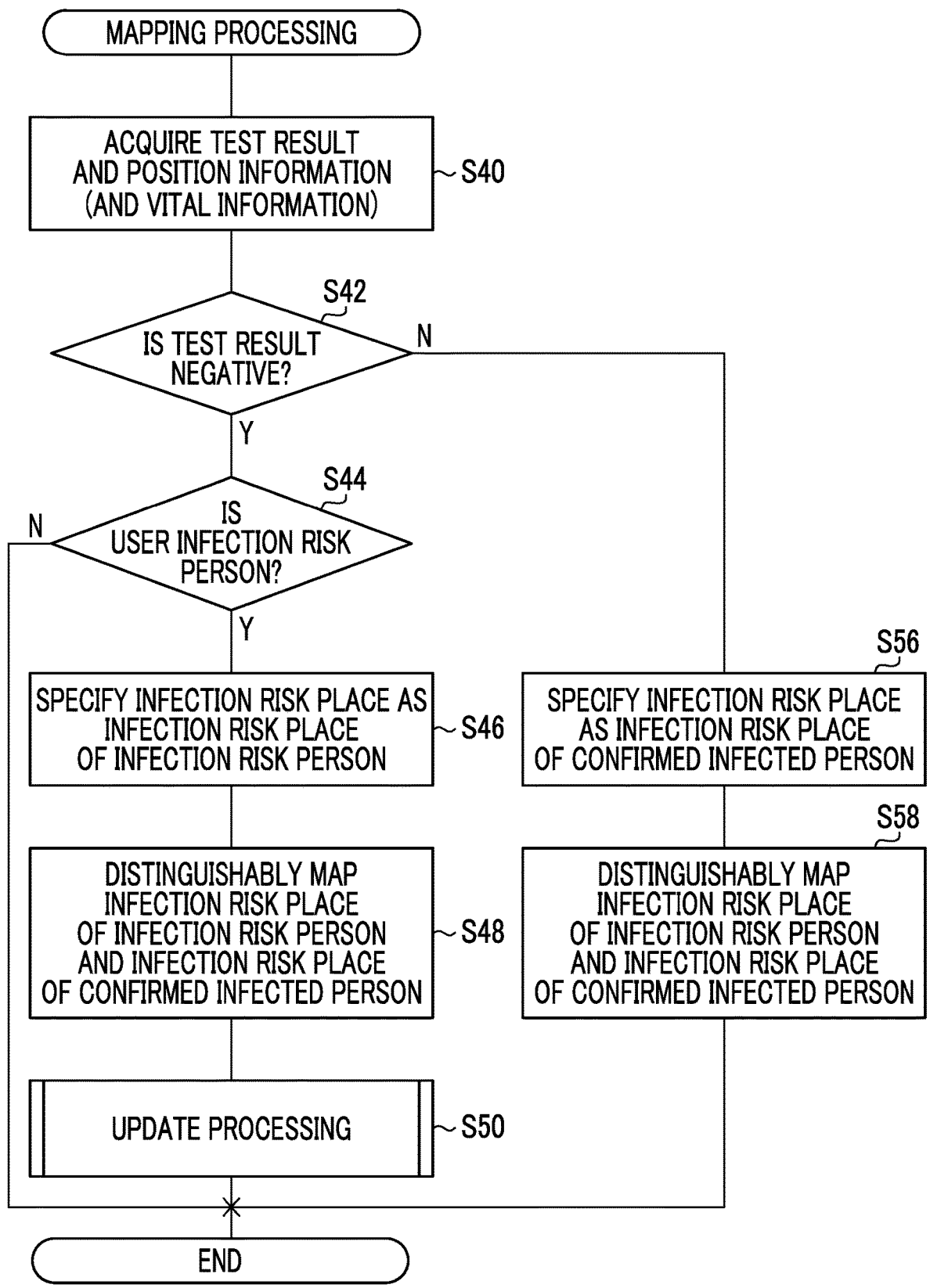
FIG. 10 is a flowchart showing an example of mapping processing in the information processing device.

Next, an action of the information processing device 10 according to the present embodiment will be described with reference to FIG. 10. In the information processing device 10, the CPU 21 executes the information processing program 27, whereby mapping processing shown in FIG. 10 is executed. The mapping processing is executed, for example, in a case where an instruction to start execution is input by the user via the input unit 25.

In step S40, the acquisition unit 30 acquires the test result obtained by the home-use test device 4 of the user and the position information to which the time information is added, from the terminal device 2 (corresponding to step S20). In addition, the acquisition unit 30 may also acquire the vital information (corresponding to step S18). In step S42, the determination unit 32 determines whether or not the test result acquired in step S40 is negative.

In a case where the test result acquired in step S40 is negative (that is, in a case where step S42 is Y), in step S44, the determination unit 32 determines whether or not the user is the infection risk person, on the basis of the vital information acquired in step S40. In a case where the user is the infection risk person (that is, in a case where step S44 is Y), in step S46, the specification unit 34 specifies the infection risk place, on the basis of the position information acquired in step S40, and stores the infection risk place as the infection risk place of the infection risk person in the storage unit 22.

In step S48, the controller 36 distinguishably maps the infection risk place specified for the infection risk person and the infection risk place specified for the confirmed infected person, which are stored in the storage unit 22. In step S50, the CPU 21 executes update processing shown in FIG. 11 and ends the mapping processing. On the other hand, in a case where the user is not the infection risk person (that is, in a case where step S44 is N), the mapping processing ends as it is.

On the other hand, in a case where the test result acquired in step S40 is positive (that is, in a case where step S42 is N), in step S56, the specification unit 34 specifies the infection risk place, on the basis of the position information acquired in step S40, and stores the infection risk place as the infection risk place of the confirmed infected person in the storage unit 22. In step S58, the controller 36 distinguishably maps the infection risk place specified for the infection risk person and the infection risk place specified for the confirmed infected person, which are stored in the storage unit 22, and ends the mapping processing.

Figure 11:
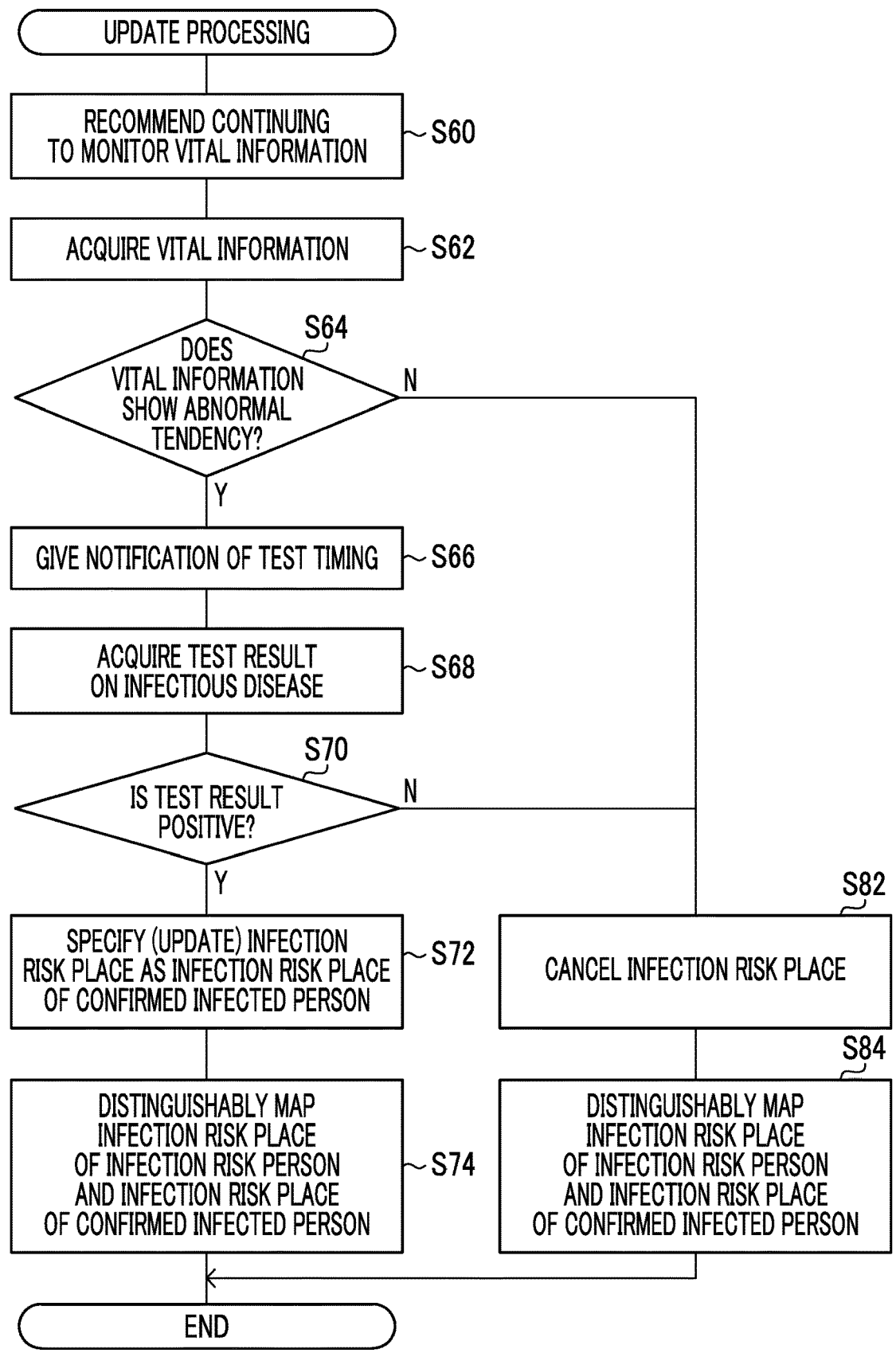
FIG. 11 is a flowchart showing an example of update processing in the information processing device.

Next, the update processing corresponding to step S50 will be described with reference to FIG. 11. That is, the update processing is processing executed in a case where the user is determined to be the infection risk person. In the information processing device 10, the CPU 21 executes the information processing program 27, whereby the update processing shown in FIG. 11 is executed.

In step S60, the controller 36 gives a notification to recommend continuing to monitor the vital information, with respect to the terminal device 2. In step S62, the acquisition unit 30 acquires the vital information, which is continuously monitored, from the terminal device 2. In step S64, the determination unit 32 determines whether or not the vital information shows the abnormal tendency, on the basis of the vital information acquired in step S62.

In a case where the vital information shows the abnormal tendency (that is, in a case where step S64 is Y), in step S66, the controller 36 notifies the terminal device 2 of the test timing for the infectious disease. In step S68, the acquisition unit 30 acquires the test result on the infectious disease of the user determined to be the infection risk person, from the home-use test device 4 or the test result management server 8. That is, this test result is the result of the test carried out at the test timing of which the terminal device 2 is notified in step S66.

In step S70, the determination unit 32 determines whether or not the test result acquired in step S68 is positive. In a case where the test result is positive (that is, in a case where step S70 is Y), in step S72, the specification unit 34 updates the information stored in the storage unit 22 so as to re-specify the infection risk place specified for the user as the infection risk place of the confirmed infected person. In step S74, the controller 36 distinguishably maps the infection risk place specified for the infection risk person and the infection risk place specified for the confirmed infected person after the update in step S72, which are stored in the storage unit 22, and ends the update processing.

On the other hand, in a case where the vital information does not show the abnormal tendency and is normal (that is, in a case where step S64 is N) and in a case where the test result is negative (that is, in a case where step S70 is N), the process proceeds to step S82. In step S82, the specification unit 34 re-specifies that the infection risk place specified for the user is not the infection risk place, and cancels the information stored in the storage unit 22. In step S84, the controller 36 distinguishably maps the infection risk place specified for the infection risk person and the infection risk place specified for the confirmed infected person after the cancel in step S82, which are stored in the storage unit 22, and ends the update processing.

As described above, the information processing device 10 according to a preferred aspect of the present disclosure comprises at least one processor, and the processor acquires the user's position information and vital information, and determines whether or not the user is the infection risk person who has a probability of infection with the infectious disease, on the basis of the vital information. In addition, in a case where the processor determines that the user is the infection risk person, the processor specifies the infection risk place where there is a probability that the user may be infected by the other person or may infect the other person, on the basis of the position information, and distinguishably maps the infection risk place specified for the infection risk person and the infection risk place specified in advance for the confirmed infected person with the infectious disease. That is, with the information processing device 10 according to the present embodiment, since the infection risk place by the infection risk person can be mapped, it is possible to contribute to the prevention of the infection spread of the infectious disease.

In the above embodiment, the aspect in which the terminal processing (see FIG. 9) in the terminal device 2 is executed in a case where a contact notification that the user has a contact probability with the infected person with COVID-19 is received from the contact history management server 6 has been described. That is, this means that the mapping processing shown in FIG. 10 is executed for a user who has a history of contact with the confirmed infected person with the infectious disease, as a target. In this case, the amount of processing can be reduced as compared with a case where the mapping processing shown in FIG. 10 is executed for all users. However, the technique of the present disclosure is applicable even in a case where the user has no probability of contact with the infected person with COVID-19.

Further, in the above embodiment, the aspect in which the user to be processed by the information processing device 10 has already carried out the self-test using the home-use test device 4 has been described, but the present disclosure is not limited thereto. The information processing device 10 can target a user who does not test whether or not the user is infected with the infectious disease and who is uncertain whether or not the user is infected with the infectious disease. In this case as well, the determination unit 32 determines, in a case where the user has a probability of infection with the infectious disease, that the user is the infection risk person on the basis of the vital information.

Further, in the above embodiment, the aspect in which the specification unit 34 specifies the infection risk place of the confirmed infected person has been described, but the present disclosure is not limited thereto. The infection risk place of the confirmed infected person may be specified in advance in, for example, an external server (not shown) that manages the behavior history of the confirmed infected person, and the acquisition unit 30 may acquire the infection risk place from the external server via the network 9.

Further, in the above embodiment, the aspect in which the determination unit 32 determines whether or not the user is the infection risk person, on the basis of the heart rate variability as an example of the vital information, has been described, but the present disclosure is not limited thereto. For example, it is known that the infected person with COVID-19 may have a tendency to increase the resting heart rate during the incubation period. In that respect, the determination unit 32 may determine whether or not the user is the infection risk person, on the basis of the resting heart rate as an example of the vital information. Further, for example, it is known that the infected person with COVID-19 may develop sleep apnea syndrome. In that respect, the determination unit 32 may determine whether or not the user has a probability of sleep apnea syndrome, on the basis of SpO2 as an example of the vital information, and determines that the user is the infection risk person in a case where the user has a probability of sleep apnea syndrome. Further, for example, the determination unit 32 may determine whether or not the user is the infection risk person by appropriately combining these plurality of types of vital information.

Further, in the above embodiment, the aspect in which the specification unit 34 specifies a place where the infection risk person has existed for a predetermined period or longer, as the infection risk place, has been described, but the predetermined period can be appropriately changed. For example, the specification unit 34 may specify a place where an infection risk person who does not wear a mask has existed, as the infection risk place, even with a shorter stay period than that of an infection risk person who wears a mask. In this case, the specification unit 34 may determine whether or not the infection risk person wears a mask by analyzing a moving image captured by a camera. Further, for example, the specification unit 34 may specify the restaurant, as the infection risk place, even with a shorter stay period than those of other places.

Further, in the above embodiment, the aspect (see FIG. 6) in which the specification unit 34 specifies the infection risk place in a unit of a building on the basis of the position information of the user has been described, but the present disclosure is not limited thereto. For example, the specification unit 34 may specify the infection risk place in a unit of a tool or equipment that can be contacted by an unspecified number of people. Examples of such a tool or equipment include benches, public toilets, playsets in parks, and automatic teller machines (ATMs). In this case, the specification unit 34 may specify the tool or equipment that is contacted by the infection risk person, as the infection risk place, by analyzing the moving image captured by the camera and through, for example, a known contact detection method using EM-Sense, a beacon, or the like.

Further, in the above embodiment, the controller 36 may give a notification to recommend cleaning the infection risk place. The notification destination in this case may be, for example, an external device owned by a management company, a cleaning company, or the like of a place that may be the infection risk place, which is predetermined for each place. According to such an aspect, prompt cleaning can be recommended, so that it is possible to contribute to the prevention of the infection spread of the infectious disease.

Further, in the above embodiment, the aspect (see FIG. 8) in which the controller 36 changes the form of the mapping of the infection risk place according to the number of confirmed infected persons and infection risk persons has been described, but the present disclosure is not limited thereto. For example, the controller 36 may change the form of the mapping of the infection risk place according to the elapsed time from the time when the infection risk person has existed at the infection risk place to the current time, on the basis of the time information. In the case of COVID-19, it is known that most of the incubation period is about 5 days, and the maximum is about 14 days. In that respect, the controller 36 may emphasize and map the infection risk place in a case where the elapsed time from the time when the infection risk person has existed at the infection risk place to the current time is zero to five days. Further, the controller 36 may cancel the mapping in a case where the elapsed time from the time when the infection risk person has existed at the infection risk place to the current time exceeds 14 days.

Further, for example, the controller 36 may change the form of the mapping of the infection risk place according to whether or not to clean the infection risk place, such as emphasizing and mapping the uncleaned infection risk place rather than the cleaned infection risk place. Further, for example, the controller 36 may change the form of the mapping of the infection risk place according to the length of the period during which the vital information of the infection risk person shows the abnormal tendency.

Further, for example, the controller 36 may emphasize and map the infection risk place of the infection risk person rather than the infection risk place of the confirmed infected person. This is because, as shown in FIG. 2, the infectivity of COVID-19 to the other person peaks before the infected person develops the disease. That is, this is because it is considered that the infection risk person has a higher infectivity to the other person than that of the confirmed infected person.

Further, for example, the controller 36 may change the form of the mapping of the infection risk place according to whether or not the infection risk person wears a mask, such as emphasizing and mapping the infection risk place of the infection risk person who does not wear a mask. In this case, the controller 36 may determine whether or not the infection risk person wears a mask by analyzing the moving image captured by the camera. Further, for example, the specification unit 34 may specify a place where the infection risk person who does not wear a mask has existed, as the infection risk place, even for a shorter stay time.

In each of the above embodiments, for example, the following various processors can be used as the hardware structure of a processing unit that executes various types of processing, such as the acquisition unit 30, the determination unit 32, the specification unit 34, and the controller 36. The above-described various processors include, for example, a programmable logic device (PLD) which is a processor having a changeable circuit configuration after manufacture, such as a field programmable gate array (FPGA), and a dedicated electrical circuit which is a processor having a dedicated circuit configuration designed to perform specific processing, such as an application specific integrated circuit (ASIC), in addition to the CPU which is a general-purpose processor that executes software (programs) to function as various processing units, as described above.

One processing unit may be composed of one of these various processors or a combination of two or more processors of the same type or different types (for example, a combination of a plurality of FPGAs or a combination of a CPU and an FPGA). Alternatively, a plurality of processing units may be composed of one processor.

A first example in which a plurality of processing units are composed of one processor is an aspect in which one or more CPUs and software are combined to constitute one processor and the processor functions as the plurality of processing units, as typified by a computer, such as a client and a server. A second example is an aspect in which a processor that realizes all the functions of a system including the plurality of processing units with one integrated circuit (IC) chip is used, as typified by a system on chip (SoC). As described above, various processing units are formed of one or more of the above-described various processors as the hardware structure.

Further, as the hardware structure of these various processors, more specifically, an electric circuit (circuitry) in which circuit elements, such as semiconductor elements, are combined can be used.

Further, in each of the above embodiments, the aspect in which the information processing program 27 is stored (installed) in the storage unit 22 in advance has been described, but the present disclosure is not limited thereto. The information processing program 27 may be provided in a form of being recorded on a recording medium, such as a compact disc read only memory (CD-ROM), a digital versatile disc read only memory (DVD-ROM), and a Universal Serial Bus (USB) memory. Alternatively, the information processing program 27 may be downloaded from an external device via the network. Furthermore, the technique of the present disclosure extends to a storage medium on which the information processing program is non-temporarily stored, in addition to the information processing program.

In the technique of the present disclosure, the above examples of embodiments can be appropriately combined with each other. The contents described and shown above are detailed descriptions of the parts related to the technique of the present disclosure, and are merely an example of the technique of the present disclosure. For example, the descriptions for the above configurations, functions, operations, and effects are the descriptions for an example of the configurations, functions, operations, and effects of parts related to the technique of the present disclosure. Accordingly, it goes without saying that an unnecessary part may be deleted, a new element may be added, or replacement may be made with respect to the contents described and shown above, within the scope not departing from the gist of the technique of the present disclosure.

EXPLANATION OF REFERENCES

1: information processing system
2, 2A to 2C: terminal device 3, 3A to 3C: measurement device
4, 4A to 4C: home-use test device
6: contact history management server
8: test result management server
9: network
10: information processing device
21: CPU
22: storage unit
23: memory
24: display
25: input unit
26: network I/F
27: information processing program
28: bus
30: acquisition unit
32: determination unit
34: specification unit
36: controller
90: map
92, 94: notification
96: warning
D1, D2: screen

What is claimed is:

1. An information processing device comprising:
at least one processor,
wherein the processor
acquires position information and vital information of a user,
determines whether or not the user is an infection risk person who has a probability of infection with an infectious disease, on the basis of the vital information,
specifies, in a case where the user is determined to be the infection risk person, an infection risk place where there is a probability that the user is infected by an other person or infects the other person, on the basis of the position information, and
distinguishably maps the infection risk place specified for the infection risk person and the infection risk place specified in advance for a confirmed infected person with the infectious disease so that the infection risk person and the confirmed infected person are distinguished.

2. The information processing device according to claim 1,
wherein the infection risk person is a person who is unaware of a symptom related to the infectious disease.

3. The information processing device according to claim 1,
wherein the infection risk person is a person who is tested for the infectious disease and who has a negative test result.

4. The information processing device according to claim 1,
wherein the infection risk person is a person who has a history of contact with the confirmed infected person with the infectious disease.

5. The information processing device according to claim 1,
wherein time information indicating a time when the user has existed at a position indicated by the position information is added to the position information, and
the processor
specifies a place where the infection risk person has existed for a predetermined period or longer as the infection risk place related to the infection risk person, on the basis of the position information and the time information.

6. The information processing device according to claim 1,
wherein time information indicating a time when the user bas existed at a position indicated by the position information is added to the position information, and
the processor
changes a form of the mapping of the infection risk place specified for the infection risk person according to an elapsed time from a time when the infection risk person has existed at the infection risk place to a current time, on the basis of the time information.

7. The information processing device according to claim 1,
wherein the processor
acquires a test result on the infectious disease of the user determined to be the infection risk person, and
updates, in a case where the user has a positive test result, the mapping of the infection risk place specified for the user to the mapping as the infection risk place of the confirmed infected person.

8. The information processing device according to claim 1,
wherein the processor
acquires a test result on the infectious disease of the user determined to be the infection risk person, and
cancels, in a case where the user has a negative test result, the mapping of the infection risk place specified for the user.

9. The information processing device according to claim 1,
wherein the processor
recommends continuing to monitor the vital information in a case where the user is determined to be the infection risk person.

10. The information processing device according to claim 1,
wherein the processor
gives a notification of a test timing for the infectious disease on the basis of the vital information, in a case where the user is determined to be the infection risk person.

11. The information processing device according to claim 1,
wherein the processor
recommends cleaning the infection risk place.

12. The information processing device according to claim 1,
wherein the processor
issues a warning in a case where the user approaches the infection risk place, on the basis of the position information.

13. The information processing device according to claim 1,
wherein the vital information indicates at least one of a heart rate variability, a heart rate, or an arterial blood oxygen saturation.

14. The information processing device according to claim 1,
wherein the processor is further configured to display a map to which the infection risk place specified for the infection risk person and the infection risk place specified in advance for the confirmed infected person with the infectious disease are distinguishably mapped on a display of a terminal device of the user in response to a request from the user.

15. An information processing method comprising:
acquiring position information and vital information of a user;
determining whether or not the user is an infection risk person who has a probability of infection with an infectious disease, on the basis of the vital information;
specifying an infection risk place where there is a probability that the user is infected by an other person or infects the other person, on the basis of the position information, in a case where the user is determined to be the infection risk person; and
distinguishably mapping the infection risk place specified for the infection risk person and the infection risk place specified in advance for a confirmed infected person with the infectious disease so that the infection risk person and the confirmed infected person are distinguished.

16. A non-transitory computer-readable storage medium storing an information processing program for causing the computer to execute a process comprising:
acquiring position information and vital information of a user;
determining whether or not the user is an infection risk person who has a probability of infection with an infectious disease, on the basis of the vital information;
specifying, in a case where the user is determined to be the infection risk person, an infection risk place where there is a probability that the user is infected by an other person or infects the other person, on the basis of the position information; and
distinguishably mapping the infection risk place specified for the infection risk person and the infection risk place specified in advance for a confirmed infected person with the infectious disease so that the infection risk person and the confirmed infected person are distinguished.

17. The information processing device according to claim 1,
wherein distinguishably mapping includes mapping by making at least one of shape, size, color, and line type of symbols different between a symbol representing information on the infection risk person and a symbol representing information on the confirmed infected person.

18. The information processing device according to claim 17,
wherein distinguishably mapping includes placing separately each of at least one symbol representing information on the infection risk person and each of at least one symbol representing information on the confirmed infected person.

19. The information processing device according to claim 18,
wherein distinguishably mapping includes making at least one of the shape, the size, the color, and the line type of the symbols different according to a number of infection risk people or the confirmed infected people corresponding to the symbols.

* * * * *